(12) United States Patent
Jain et al.

(10) Patent No.: US 8,551,451 B2
(45) Date of Patent: Oct. 8, 2013

(54) COMBINATION VACCINE WITH ACELLULAR PERTUSSIS

(75) Inventors: Rajesh Jain, New Delhi (IN); Sukhjeet Singh, New Delhi (IN); Lavit Jambu, New Delhi (IN)

(73) Assignee: Panacea Biotec Limited, New Delhi (IN)

( * ) Notice: Subject to any disclaimer, the term of this patent is extended or adjusted under 35 U.S.C. 154(b) by 84 days.

(21) Appl. No.: 13/125,708

(22) PCT Filed: Oct. 23, 2009

(86) PCT No.: PCT/IN2009/000600
§ 371 (c)(1),
(2), (4) Date: Apr. 22, 2011

(87) PCT Pub. No.: WO2010/046935
PCT Pub. Date: Apr. 29, 2010

(65) Prior Publication Data
US 2011/0206726 A1    Aug. 25, 2011

(30) Foreign Application Priority Data
Oct. 24, 2008  (IN) .......................... 2438/DEL/2008

(51) Int. Cl.
*A61K 49/00* (2006.01)
*A61K 39/00* (2006.01)
*A61K 39/02* (2006.01)

(52) U.S. Cl.
USPC ....... 424/9.2; 424/9.1; 424/184.1; 424/201.1; 424/203.1; 424/238.1; 424/239.1; 424/256.1

(58) Field of Classification Search
USPC ................. 424/9.1, 9.2, 184.1, 201.1, 203.1, 424/238.1, 239.1, 256.1
See application file for complete search history.

(56) References Cited

U.S. PATENT DOCUMENTS

| 5,877,298 A | 3/1999 | Fahim et al. |
| 6,013,264 A | 1/2000 | Petre et al. |
| 6,333,036 B1 | 12/2001 | Arminjon et al. |
| 6,756,040 B2 | 6/2004 | Peetermans et al. |

FOREIGN PATENT DOCUMENTS

| EP | 1 967 204 | 9/2008 |
| WO | WO 98/00167 | 1/1998 |
| WO | WO 99/13906 | 3/1999 |
| WO | WO 2004/110480 | 12/2004 |
| WO | WO 2005/089794 | 9/2005 |
| WO | WO 2007/054820 | 5/2007 |

OTHER PUBLICATIONS

Papavenagelou, George, "Current Combined Vaccines with Hepatitis B", Vaccine 16, (1998) pp. S69-S72.
Kanra, Guler, et al., "Effect of Aluminum Adjuvants on Safety and Immunogenicity of *Haemophilus influenzae* Type b-CRM 197 Conjugate Vaccine", Pediatrics International (2003) 45, pp. 314-318, XP-002354341.

*Primary Examiner* — Rodney P. Swartz
(74) *Attorney, Agent, or Firm* — Lowe Hauptman & Ham, LLP

(57) ABSTRACT

The present invention relates to a combination vaccine comprising a mixture of antigens for protection against diseases such as diphtheria, tetanus, acellular pertussis, and infections caused by *Haemophilus influenzae* and polio viruses. The present invention also relates to inclusion of antigens for protection against infections caused Hepatitis virus and other pathogens, such that administration of the vaccine can simultaneously immunize a subject against more than one pathogen. The invention in particular relates to a fully liquid stable combination vaccine comprising the antigens as indicated above and the methods for manufacturing the same.

28 Claims, No Drawings

COMBINATION VACCINE WITH ACELLULAR PERTUSSIS

CROSS-REFERENCE TO RELATED APPLICATIONS

The present Application is the U.S. National Stage of International Application No. PCT/IN2009/000600, filed on Oct. 23, 2009, published in English; which Application claims priority benefit of Indian Application No. 2438/DEL/2008, filed on Oct. 24, 2008.

FIELD OF INVENTION

The present invention relates to a combination vaccine comprising a mixture of antigens for protection against diseases such as diphtheria, tetanus, pertussis, and infections caused by *Haemophilus influenzae* and polio viruses. The present invention also relates to inclusion of antigens for protection against infections caused by Hepatitis virus and other pathogens, such that administration of the vaccine can simultaneously immunize a subject against more than one pathogen. The invention in particular relates to a fully liquid stable combination vaccine comprising the antigens as indicated above and the methods for manufacturing the same.

BACKGROUND OF THE INVENTION

Antigens Vaccine
Diphtheria and Tetanus Antigens

Diphtheria and tetanus are acute infections caused by *Corynebacterium diphtheriae* and *Clostridium tetani*, respectively. The toxins of these bacteria are the major cause of the respective diseases. The vaccines affording protection against these bacteria contain these toxins that are toxoided to lose their infectivity. The toxins are treated using chemicals such as formaldehyde or glutaraldehyde for making toxoids [diphtheria toxoid (DT) and Tetanus toxoid (TT)]. CRM 197, a mutant diphtheria toxin, is also used in certain vaccines.

Pertussis Antigens

The whooping cough disease or the pertussis is caused by *Bordetella pertussis*. This is a debilitating and serious disease that may even lead to death. The initial vaccines against the disease were based on the whole cells which were treated with chemicals such as formaldehyde to kill the cells and inactivate the toxic materials. Though highly efficacious, such vaccines called as the 'whole cell (wP) vaccines', were associated with side effects including fever and local reactions. The need for a more defined vaccine was recognized and the researchers then changed the focus to the development of a vaccine comprising lesser number of highly purified antigens, called the 'component vaccine'. Many virulence associated factors such as the pertussis toxin (PT), filamentous hemagglutinin (FHA), pertactin (PRN or P69), fimbrial proteins (FIM 1, 2 and 3), adenyl cyclase, lipopolysaccharide and other outer membrane proteins have been suggested for the inclusion in the 'acellular vaccine', which is less defined as compared to component vaccine. Much of the work has been concentrated on PT based vaccine which was only partially protective. A combination of PT/FHA was more efficacious but still had lesser immunogenicity than the wP based vaccine. Another potential candidate, PRN or P69, was found to make the pertussis vaccine more effective in combination with PT and FHA. Certain pertussis vaccine also had FIM as the fourth partner imparting immunogenicity against pertussis.

Poliomyelitis Antigens

Two different kinds of vaccine are available:

A live attenuated (weakened) oral polio vaccine (OPV) developed by Dr. Albert Sabin in 1961. OPV, comprising the Sabin strains, is given orally.

An inactivated (killed) polio vaccine (IPV) developed in 1955 by Dr. Jonas Salk, IPV, comprising the Salk strains, is given as an injection.

Both live attenuated (OPV) and inactivated (IPV) polio vaccines have been effective in controlling the polio disease worldwide. The polio vaccine may comprise the Salk or the Sabin strains. Mahoney type 1, MEF Type 2 and the Saukett type 3 are the Salk strains that have been used in the vaccine against the poliomyelitis disease. The Sabin strains include the Sabin 1 and Sabin 2 strains.

*Haemophilus influenzae* (Hib) Antigens

*Haemophilus influenzae* is a Gram-negative coccobacillus that is a normal part of upper respiratory tract flora. *Haemophilus influenzae* type b (Hib b) is a major cause of invasive bloodborne infections in young children and major cause of meningitis in the first 2 years of life. Immunization against *Haemophilus influenzae* began in Canada in 1987 with a polysaccharide vaccine [polyribose ribitol phosphate (PRP)]. The polyribosylribitol phosphate (PRP) capsule of Hib is a major virulence factor for the organism. Antibody to PRP is the primary contributor to serum bactericidal activity, and increasing levels of antibody are associated with decreasing risk of invasive disease, PRP is a T-cell independent antigen and hence is characterized by a) induction of a poor antibody response in less than 18-month-old infants and children, b) a variable and quantitatively smaller antibody response than that seen with T-cell dependent antigens, c) production of a higher proportion of immunoglobulin M (IgM), and d) inability to induce a booster response.

The initial vaccines based only on the PRP component proved to be ineffective in the infants. Further efforts were directed towards the PRP conjugate vaccine, wherein the PRP is conjugated to proteins called the carrier proteins such as the outer membrane protein of *Neisseria meningitides*, diphtheria toxoid, tetanus toxoid and CRM 197.

Hepatitis (Hep) Antigens

There are various strains of Hepatitis virus. Hepatitis B is a disease caused by hepatitis B virus (HBV) which infects the liver of hominoidae, including humans, and causes an inflammation called hepatitis. It ranges in severity from a mild illness, lasting a few weeks (acute), to a serious long-term (chronic) illness that can lead to liver disease or liver cancer. The vaccine against the disease contains a viral envelope protein, hepatitis B surface antigen (HBsAg). The FDA approved Hep B containing vaccines are Recombivax HB® and Comvax® by Merck, Engerix-B® and Pediarix® by GlaxoSmithKline Biologicals.

Other Antigens

The other antigens that the human race is concerned with include *Haemophilus influenzae* (a, c, d, e, f serotypes and the unencapsulated strains), Hepatitis (A, C, D, E, F and G strains), meningitis A, B or C, Influenza, Pneumococci, Streptococci, anthrax, dengue, malaria, measles, mumps, rubella, BCG, Japanese encephalitis, Rotavirus, smallpox, yellow fever, typhoid, Singles, Varicella, and others.

Combination Vaccines

In spite of the long decades of research in the field of vaccines, the infectious diseases remain a threat to the human kind. Combination vaccines that protect against various diseases are very desirable since it reduces the number of shots given, reduces the administration and production costs and improves the patient compliance as well. Such combination vaccines are generally better accepted.

However, the well documented phenomenon of the antigenic competition has complicated and hindered the development of the multivalent vaccines. This phenomenon refers to the observation that administering multiple antigens together often results in a diminished response to certain antigens relative to the immune response to these antigens when administered separately.

The earlier research has been focused on the development of the vaccine with multiple valencies directed towards different diseases and infections. One such well known vaccine combination is one that provides protection against diphtheria, tetanus and acellular pertussis. The acellular pertussis (aP) component normally comprises 2 or all 3 of the detoxified PT (pertussis toxin), FHA (filamentous haemagglutinin) and PRN or P69 (pertactin). In some cases, other pertussis antigens such as the fimbriae antigens (Fim 1, 2 or 3) may also be present.

Infanrix® (GlaxoSmithKline Biologicals), Tripedia® and Daptacel® (Sanofi Pasteur) are the FDA approved DTaP combination vaccines.

It is desirable to add other antigens to such a combination vaccine that would give protection against diseases caused by Hepatitis virus (Hep), *Haemophilus influenzae* (Hib) and polioviruses (IPV). It is also desirable to have antigens providing protection against other diseases added to the above said combination vaccines.

A recently FDA approved vaccine Kinrix® by GlaxoSmithKline Biologicals, is a combination vaccine that has IPV along with DTaP (Infanrix®) antigens. Infanrix-Hib® is another combination provided by GlaxoSmithKline Biologicals wherein the DTaP antigens are present in a liquid form and the Hib antigen is lyophilized and supplied in a separate vial. Pediarix® and Infanrix Penta® by GlaxoSmithKline Biologicals comprises a single vial dose combination vaccine that comprises DTaP along with the Hep B and the IPV component. The Pentacel® by Sanofi Pasteur is a combination of five vaccine components supplied as DTaP-IPV in liquid form and the Hib component in a dried form. The Infanrix Hexa® is a six component combination vaccine by GlaxoSmithKline Biologicals, that protects against the diseases such as diphtheria, tetanus, pertussis, polio, and infections caused by Hep B virus and *Haemophilus influenzae* type b. Even in this combination all the components except the Hib component are present in liquid form, the Hib component being present in the lyophilized form. Thus, none of the above given combination vaccines are marketed as a fully liquid formulations and comprise antigens such as Hib and Hep along with the antigens providing protection against diphtheria, tetanus, pertussis and polio, in a single vial.

U.S. Pat. No. 6,756,040 states that simple mixing of the vaccine components results in reduction in the antibody titres to the polysaccharide component, due to antigenic interference. US'040 relates to a vaccine formulation for the prevention of *Haemophilus influenzae* (Hib) Type b infections wherein there is a requirement that the Hib b conjugate is adsorbed on to aluminium phosphate so as to inhibit the reduction of anti-polysaccharide antibodies. Further, the Hib b antigen is lyophilized and mixed with the other antigens present in liquid form, no more than one hour before administration. Thus, there is no teaching in U.S. Pat. No. '040 of a combination vaccine which is present as a fully liquid formulation and comprises the antigens affording protection against diphtheria, tetanus, pertussis and infections caused by *Haemophilus influenzae*, hepatitis and polio viruses.

U.S. Pat. No. 6,013,264 by SmithKline Beecham Biologicals relates to a multivalent vaccine comprising HBsAg (Hep B antigen) adsorbed on to aluminium phosphate. It advocates that when aluminium hydroxide adsorbed HBsAg is used in a combination vaccine, there is a significant decrease in the immune response to the HBsAg component resulting in insufficient seroconversion after vaccination. It further states that there is a need of avoiding the use of aluminium hydroxide as an adjuvant for adsorption of HBsAg in a multivalent vaccine. The specification states that the b component may be added extemporaneously to the vaccine of the invention. Thus, there is no teaching in US'264 of a combination vaccine which is present as a fully liquid formulation and comprises the antigens affording protection against diphtheria, tetanus, pertussis and infections caused by *Haemophilus influenzae*, hepatitis and polio viruses. Also the vaccine according to US'264 has a specific requirement that the Hep B antigen be adsorbed on to aluminum phosphate and not on to aluminum hydroxide.

PCT Application WO2007054820 by Novartis Vaccines and Diagnostics relates to a vaccine composition wherein the D and the T antigens are specifically adsorbed on to aluminum hydroxide and the Hib b and the Hep B antigens are adsorbed on to aluminum phosphate. This application however, does not teach the preparation of fully liquid stable combination vaccine wherein the D, T and the aP antigens are adsorbed on to aluminum phosphate and the Hep antigen is adsorbed on to aluminum hydroxide.

PCT Application WO1998000167A1 by Connaught Lab provides a multivalent immunogenic composition for conferring protection in a host against disease caused by infections by *Bordetella pertussis, Clostridium tetani, Corynebacterium diphtheriae*, Poliovirus and/or *Haemophilus influenzae*. The Hib b component of the vaccine, according to the specification is a lyophilized component that has to be reconstituted before mixing with the other components of the vaccine. Thus, there is no teaching in the specification related to a fully liquid combination vaccine comprising all the said antigens.

Lyophilization, also called as freeze drying, is a cost-intensive process that also causes a lot of stress to the proteins. When any component of the vaccine is lyophilized, at the time of administration of the vaccine, it is required to mix the lyophilizate with another liquid or the liquid component of the combination vaccine. This represents a supplementary constraint for the practitioner and presents a risk of it being carried out badly. It was then proposed to have a multi compartment syringe that would have the lyophilized component in one compartment and the liquid component of the vaccine in the other. However, such a syringe whose contents could be mixed at the time of administration of the vaccine, does not perform satisfactorily at the level of reducing the production costs as well as at the level of the operations to be carried out by the practitioner.

It is hence desirable to avoid this step of freeze drying and provide a combination vaccine that has all the components present together and in fully liquid form. This would facilitate the administration of the vaccine, make it patient compliant and also reduce the production costs. It is thus desirable to have the Hib antigen added to the liquid component of the vaccine and thus have a fully liquid multivalent vaccine.

PCT Application WO2004110480 by Glaxo SmithKline Biologicals relates to a vaccine comprising Hib b polysaccharide. The application states that simple mixing of the components of a combination vaccine is complicated by the fact that not all antigens can be effectively mixed together. It states that there is interference between the aluminium hydroxide of the DTP vaccine and PRP. The invention in WO'480 aims at minimizing this interference in such an extemporaneously-prepared combination vaccine wherein the PRP is pre-adsorbed onto aluminum phosphate. The invention further provides immunogenic compositions, vaccines and combination vaccines comprising PRP which is protected to some degree from immune interference. The inventors have found that the above can be achieved by incorporating a polyanionic polymer excipient with the vaccine comprising PRP.

However, use of the polyanionic polymer in the vaccine formulation may not be desirable as it may increase the cost of formulating the vaccine. Also, since a vaccine is finally intended for human use, it should ideally have the least components possible. The use of additional ingredients means addition of substances to the formulation to which the body may react and produce antibodies. Such a response of the body corning in contact with such components of the immunological preparation may not be desirable.

U.S. Pat. No. 6,333,036 by Pasteur Merieux Serums relates to vaccine compositions comprising capsular polysaccharide of *Haemophilus influenzae* type b or high molecular weight polyribosylribitol phosphate (PRP) coupled to tetanus anatoxin, as well as an aluminium-based adjuvant. The aluminium based adjuvants used in the invention have a point of zero charge of less than approximately 7.2. The patent however, does not particularly teach the preparation of a combination vaccine comprising antigens affording protection against diphtheria, tetanus, pertussis and infections caused by *Haemophilus influenzae* and polio viruses, in fully liquid form, wherein the Hib antigen may not be substantially adsorbed on to any adjuvant. This patent also does not teach preparation of a fully liquid stable combination vaccine comprising antigens affording protection against diphtheria, tetanus, pertussis and infections caused by *Haemophilus influenzae*, Hepatitis and polio viruses, wherein the diphtheria, tetanus and the pertussis antigens are adsorbed on to aluminum phosphate and the Hepatitis antigen is adsorbed on to aluminum hydroxide.

European Patent 1028750 by Sanofi Pasteur MSD, relates to a multivalent vaccine conferring protection in against diseases caused by *Bordetella pertussis, Corynebacterium diphiheriae, Clostridium tetani*, Polioviruses, Hepatitis B virus and *Haemophilus influenzae*. The patent however, does not particularly teach the preparation of a combination vaccine comprising antigens affording protection against diphtheria, tetanus, pertussis and infections caused by *Haemophilus influenzae*, hepatitis and polio viruses, in fully liquid form, wherein the D, T and the aP antigens are adsorbed on to aluminum phosphate and the Hep antigen is not adsorbed on to aluminum hydroxide.

Hexavac® by Aventis Pasteur MSD is a fully liquid vaccine approved for protection against the diseases caused by the said organisms. This vaccine however, was suspended from use worldwide due to post marketing issues on account of variability in the production process for the vaccine's hepatitis B component that could lead to a decreased long-term protection against hepatitis B.

Though, the research is ongoing for making multivalent vaccine comprising various antigens that would afford protection against a number of diseases, they have not addressed the need for providing a stable combination vaccine comprising antigens affording protection against diphtheria, tetanus, pertussis and infections caused by *Haemophilus influenzae* and polio viruses, in fully liquid form, wherein the Hib antigen may not be substantially adsorbed on to any adjuvant. Also there no disclosure of making a stable combination vaccine comprising antigens affording protection against diphtheria, tetanus, pertussis and infections caused by *Haemophilus influenzae*, hepatitis and polio viruses, in fully liquid form, wherein D, T and the aP antigens are adsorbed on to aluminum phosphate and the Hep antigen is adsorbed on to aluminum hydroxide. There are contrasting reports available regarding the antibody responses against particular antigens in children immunized by separate and co-administration of the combination vaccines and the PRP vaccine. There may be various reasons for such results including the vaccines being non-identical in their antigenic content, method of toxoiding, adjuvantation or the preservative used.

Thus, the currently commercially-available combination vaccines may not contain appropriate formulations of appropriate antigens in appropriate immunogenic forms for achieving desired levels of efficacy and immunogenicity in the susceptible human population, for a number of diseases in one shot. There is a need for a multi component vaccine that provides protection against various infections and is in liquid form so as to afford ease of administration and comfort of cost-effectiveness. It would be desirable to provide for a stable and efficacious multivalent vaccine against diseases caused by the infection caused by *Corynebacterium diphtheria, Clostridium tetani, Bordetella pertussis*, polioviruses, Hepatitis virus, *Haemophilus influenzae* and others. For such a vaccine to be effective, the criterion of seroprotection for each of the antigens of the vaccine needs to be fulfilled. For this there is a need to overcome the hurdles and the challenges posed by antigenic competition and interference. The present invention overcomes the limitations of prior arts and solves the related problems by providing a multivalent vaccine formulation protecting against a plurality of diseases.

SUMMARY OF THE INVENTION

The present invention relates to combination vaccine comprising a mixture of antigens for protection against diseases such as diphtheria, tetanus, pertussis, and infections caused by *Haemophilus influenzae* and polio viruses. The present invention also relates to inclusion of antigens for protection against infections caused by Hepatitis virus and other pathogens, such that administration of the vaccine can simultaneously immunize a subject against more than one pathogen. The invention in particular relates to a fully liquid stable combination vaccine comprising the antigens as indicated above and the methods for manufacturing the same.

The present invention further relates to a pentavalent vaccine wherein Hib antigen is not substantially adsorbed on to any adjuvant. The invention also relates to a fully liquid stable hexavalent vaccine comprising antigens affording protection against a plurality of diseases, wherein the diphtheria, tetanus and the acellular pertussis antigens are adsorbed on to aluminum phosphate and the Hepatitis antigen is adsorbed on to aluminum hydroxide.

The present invention is further directed towards a combination vaccine that comprises a plurality of the vaccine components that are suitable for the prevention, amelioration and treatment of multiple disease states that meet the criterion for the seroprotection for each of the said vaccine components.

DETAILED DESCRIPTION OF THE INVENTION

The present invention is directed towards a fully liquid stable combination vaccine that comprises a plurality of the vaccine components that are suitable for the prevention, amelioration and treatment of multiple disease states that meet the criterion for the seroprotection for each of the said vaccine components.

The advantages of the present invention include a multivalent vaccine which can confer protection against a wide range of diseases and infections in a safe and efficacious manner. The vaccine of the invention provides immunogenicity to various diseases and infections without any interference of any of the antigen that is present in the vaccine. Thus, a single shot would confer immunogenicity against various diseases and infections, making the vaccine more patients compliant. Since a single shot would afford immunity against a number of infections and diseases, the cost of vaccination would be reduced. The vaccine of the present invention would be beneficial in the sense that it will reduce the number of visits to the vaccination centre and also the number of shots to be given for a number of different diseases and infections. This aspect of the invention would make it more useful and advantageous especially with the younger population who need to be vaccinated to confer immunity to a large number of infections and diseases. Thus, the present invention provides a vaccine that is more acceptable.

Definitions

The term 'fully liquid' as used herein to describe the vaccine of the invention, refers to the state of the vaccine wherein all the components of the vaccine are in liquid state and there is no component of the vaccine that is provided in lyophilized or any other form so that it has to be mixed with the other components of the vaccine before administering it to a subject.

The term 'carrier protein' as used herein to describe the proteinic component to which the capsular polysaccharide (Hib) used in the vaccine is conjugated so as to convert the T-cell independent polysaccharide to T-cell dependent antigen.

The term 'adjuvant' as used herein to describe the non-antigenic component of the vaccine that enhances the immune response of the antigens of the vaccine by facilitating the contact between the antigen and the immune system by influencing the type and the quality of the immune response generated against an antigen. The adjuvant causes prolonged immune responses against the antigens and also may serve to decrease toxicity of certain antigens or provide solubility to certain antigens.

The term 'stable' used herein to describe the vaccine of the invention means that each of the antigens of the vaccine composition has a potency/immunogenicity more than that set as the normal acceptance limit, after the incubation of the vaccine at 5±3° C. for at least 1, preferably 12 and most preferably 24 months.

The term 'substantially' used herein to describe the amount of adsorption or coupling of the Hib on to any adjuvant, in the expression 'Hib is not substantially adsorbed on to any adjuvant', means that adsorption of Fhb on to any adjuvant is less than 15%, and preferably less than 10%. The Hib antigen is not subjected to any step so as to intentionally adsorb it on to any adjuvant; the amount of the adsorption may be happening may be due to the contact between the antigen and the adjuvant and is not deliberate.

The term of 'about' used herein to describe the amount of each of the components present in the vaccine of the invention, means an amount of the said vaccine component that is present in amounts of preferably ±20%, more preferably ±10% and most preferably ±5% of the stated amount for that particular component.

The term 'about' as used herein to describe the time of stirring of the mixture during the process of preparation of the vaccine of the invention, is preferably ±20%, more preferably ±10% and most preferably ±5% of the stated value.

The term 'immunologically active' used herein in reference to the combination vaccine of the invention means that the vaccine when administered to the subject is able to elicit antibodies against each of the antigens of the said combination so as to protect the vaccinee against the respective diseases or infections.

The term 'coupling or adsorbing' used herein with references to the antigens of the combination vaccine of the invention refers to any form of physical bonding between the antigen and the adjuvant.

The Vaccine of the Invention

The present invention provides a stable combination vaccine composition in which all the components of the vaccine are present together in liquid form in a single vial.

One aspect of the present invention provides a fully liquid stable pentavalent vaccine comprising Diptheria (P), Tetanus (T), Acellular pertussis (aP), *Haemophilus influenzae* (Hib) and Poliovirus (IPV) antigens, wherein Hib is not substantially adsorbed on to any adjuvant.

Another aspect of the present invention relates to a fully liquid stable hexavalent vaccine comprising Diptheria (D), Tetanus (T), Acellular pertussis (aP), *Haemophilus influenzae* (Hib) and Hepatitis (Rep) and Poliovirus (IPV) antigens, wherein the 1), T and the aP antigens are adsorbed on to aluminum phosphate and Rep antigen is adsorbed on to aluminum hydroxide.

The invention further provides that the diphtheria (D), Tetanus (T) and Acellular pertussis (aP) antigens are adsorbed only on to aluminum phosphate and not to aluminum hydroxide.

According to an aspect of the invention, the Hib antigen is conjugated to a carrier protein selected from a group comprising of tetanus toxoid (TT), diphtheria toxoid (DT), CRM 197 and outer membrane protein of *Neisseria meningitides* or any equivalents thereof, or any other known carriers.

According to another aspect of the invention, the Hib antigen is not substantially adsorbed on to any adjuvant.

According to another aspect of the invention, the Hib antigen in the vaccine of the invention is derived from the capsular polysaccharide of Hib b strain.

One aspect of the invention provides that the Hep antigen is adsorbed on to aluminum hydroxide and not on to aluminum phosphate.

One further aspect of the invention relates to the Hep antigen being derived from the Hepatitis B surface antigen (HBsAg); i.e. the surface antigen of the Hep B strain.

According to one other aspect of the invention, the IPV strains are one or more Salk strains which may be selected from the group of Mahoney type 1, MEF type 2 and Saukett type 3 or one or more Sabin strains selected from the group of Sabin types 1 and 2.

Another aspect of the invention provides that the vaccine of the invention comprises 2-phenoxyethanol as a preservative in the formulation.

Further, another aspect of the invention relate to the process of manufacturing the combination vaccines of the invention.

One other aspect of the invention relates to the composition of the combination vaccines of the invention such that each of the antigens is present in an amount in the vaccine so as to elicit a protective immune response against the said antigen.

Antigens of the Vaccine of the Invention

Diphtheria is caused by *Corynebacterium diphtheriae*, a Gram-positive non-sporing aerobic bacterium. This organism expresses a prophage-encoded ADP-ribosylating exotoxin (diphtheria toxin), which can be treated (e.g. using formaldehyde) to give a toxoid. This toxoid is no longer toxic but still remains antigenic and is able to stimulate the production of specific anti-toxin antibodies after injection. The Diphtheria antigen preparation used in the vaccine of the invention preferably comprises Diphtheria toxoid.

Tetanus is caused by *Clostridium tetani*, a Gram-positive, spore-forming bacillus. This organism expresses an endopeptidase ('tetanus toxin'), which can be treated to give a toxoid that is no longer toxic. However it still remains antigenic and is able to stimulate the production of specific anti-toxin antibodies after injection. The Tetanus antigen preparation used in the vaccine of the invention preferably comprises Tetanus toxoid.

Pertussis or whooping cough is caused by *Bordetella pertussis*. The acellular pertussis (aP) antigens may be obtained from any of the known *Bordetella pertussis* strains. For the purpose of the invention the aP antigens may preferably be obtained from the *B. pertussis* Tohama strain. Any of the appropriate media may be used for the isolation, culturing, proliferation and fermentation of the culture. For the purpose of the invention the modified Stainer-Scholte may preferably be used. The acellular pertussis (aP) antigens used in the vaccine of the present invention comprise at least one or more antigens selected from the group of Pertussis toxoid (PT). Filamentous hemagglutinin (FHA), Pertactin (P69 or PRN) and FIM (fimbrial antigens-1, 2 or 3). However, according to the preferred embodiment of the invention, the aP antigen preparation used in the vaccine of the invention comprises PT, FHA and PRN (P69) antigens.

*Haemophilus influenzae* is a Gram-negative coccobacillus which causes invasive bloodborne infections and meningitis. According to one embodiment of the invention, the Hib antigen, which is derived from the capsular polysaccharide, may be conjugated or coupled to carrier proteins. The carrier proteins used for the conjugation of the Hib antigen may be selected from comprising of tetanus toxoid (TT), diphtheria toxoid (DT), CRM 197 and outer membrane protein of *Neisseria meningitides* or any equivalents thereof. Other suitable carrier proteins include, but are not limited to, synthetic peptides, heat shock proteins, pertussis proteins, cytokines, lymphokines, hormones, growth factors, artificial proteins comprising multiple human CD4+ T cell epitopes from various pathogen-derived antigens such as N19, protein D from *H. influenzae*, pneumococcal surface protein PspA, pneumolysin, iron-uptake proteins, toxin A or B from *C. difficile* and *S. agalactiae* proteins. The Hib antigen preparation used in the vaccine of the invention comprises Hib antigen preferably conjugated or coupled to tetanus toxoid.

The polysaccharide conjugate may be prepared by any known coupling technique. For example the polysaccharide can be coupled via a thioether linkage. This conjugation method relies on activation of the polysaccharide with 1-cyano-4-dimethylamino pyridinium tetrafluoroborate (CDAP) to form a cyanate ester. The activated polysaccharide may thus be coupled directly or via a spacer group to an amino group on the carrier protein. The conjugates can also be prepared by direct reductive amination methods. Another method involves the coupling of a cyanogen bromide (CNBr) activated polysaccharide derivatised with adipic acid hydrazide (ADH) to the protein carrier by carbodiimide condensation. Any other known method may be used to prepare the polysaccharide conjugate used in the vaccine of the invention.

According to an embodiment of the invention, the Hib antigen is not substantially adsorbed on to any adjuvant; preferably, the degree of adsorption of the Hib antigen to an adjuvant is not more than 15%; more preferably, the degree of adsorption of the Hib antigen to an adjuvant is not more than 10%.

According to another embodiment of the invention relates to the Hib antigen not being subjected to deliberate or intentional adsorption on any adjuvant.

According to another preferred embodiment of the invention, the Hib antigen preparation comprises antigen derived from the capsular polysaccharide of the Hib b strain.

Hepatitis is caused by various Hepatitis strains such as A, B, C, D, E, F or G. Hepatitis B virus (HMV) is one of the major agents which cause viral hepatitis. The HBV virion consists of an inner core surrounded by an outer protein coat or capsid. The major component of the capsid is a protein known as HBV surface antigen or, more commonly, 'HBsAg'. When this antigen is administered to a vaccinee it stimulates the production of anti-HBsAg antibodies which protect against HBV infection. According to one preferred aspect of the invention, the Hepatitis (Rep) antigen preparation used in the vaccine of the invention comprises Hep antigens derived from the surface antigen of Hepatitis B strain (HBsAg).

For vaccine manufacture, HBsAg can be made either by purifying the antigen in particulate form from the plasma of chronic hepatitis B carriers, as large quantities of HBsAg are synthesized in the liver and released into the blood stream during an HBV infection or by expressing the protein by recombinant DNA methods. HBsAg for use in the vaccine of the invention may be prepared in either way.

Poliomyelitis is caused by the polio viruses. The vaccine of the invention may comprise Sabin (Sabin 1 and/or Sabin 2) or Salk strains of Poliovirus. According to one preferred embodiment of the invention, the vaccine of the invention comprises Salk strains. There are 3 types of Salk strains that can cause poliomyelitis. The three types are similar and cause identical symptoms, but they are antigenically very different and infection by one type does not protect against infection by others. Salk Poliovirus includes 3 strains-Type 1 (e.g. Mahoney strain), poliovirus Type 2 (e.g. MEF-I strain), and poliovirus Type 3 (e.g. Saukett strain). According to a preferred embodiment of the invention, the vaccine of the invention may comprise one or more of the said Salk strains.

Polioviruses may be grown in cell culture. Vero cell line, which is a continuous cell line derived from monkey kidney, may be used to grow the polioviruses. After growth, virions may be purified using already known techniques. The inactivation of the viruses may be done. Quantities of poliovirus are typically expressed in the 'DU' unit (the "D-antigen unit"). The IPV antigen preparation used in the manufacturing of the vaccine of the invention is preferably prepared so as to comprise one or more strains that are used in the manufacturing of the vaccine. This bulk preparation is then used to formulate the vaccine of the invention.

Non-Antigenic Components of the Vaccine

Along with the antigenic components the vaccine may comprise a number of non-antigenic components that are pharmaceutically acceptable excipients. These include but are not restricted to pH modifiers, buffers, adjuvants, preservative, carrier and tonicity modifying agents.

Adjuvants

The antigens of the final formulation may or may not be adsorbed on to an adjuvant. An adjuvant functions to stimulate the production of immunity against the vaccine ingredients, making the vaccine more effective.

Adjuvants may serve to:

Bring the antigen in contact with the immune system and influence the type of immunity produced, as well as the quality of the immune response (magnitude or duration);

Decrease the toxicity of certain antigens; and

Provide solubility to some vaccines components.

Studies have shown that many aluminum-containing vaccines cause higher and more prolonged antibody responses than comparable vaccines without the adjuvant. The benefit of adjuvants has usually been observed during the initial immunization series rather than with booster doses.

Aluminum based adjuvants are the most commonly used adjuvants. These adjuvants have also been approved by FDA for use in vaccines. There are three general types of aluminum-containing adjuvants:

Aluminum hydroxide
Aluminum phosphate
Potassium aluminum sulfate (often called "Alum")

One embodiment of the invention relates to certain antigens of the vaccine being adsorbed on to aluminum phosphate and certain antigens of the vaccine being adsorbed on to aluminum hydroxide. Certain antigens may be adsorbed only on to aluminum phosphate and not on to aluminum hydroxide and vice versa. Certain antigens of the invention may not be adsorbed at all or substantially adsorbed on to any adjuvant. The preference of the adjuvant for the adsorption of the said antigens gives the vaccine of the invention its characteristics. The preference of adsorption is described in more details in the section on 'Process for manufacturing of the vaccine of the invention', below.

Preservatives

The vaccines are prone to contamination by bacteria. Thus, to avoid the potentially life threatening contamination with harmful microbes, that may be introduced in a vaccine incorporated during the event of accidental contamination, a preservative may be included in the composition of the vaccine while formulating it. The preservatives that have been used include Benzethonium chloride (Phemerol), thiomersal, Phenol and 2-phenoxyethanol (2-POE).

Thimerosal is a mercury-containing organic compound (an organomercurial) that has been used in many vaccines as a preservative. There are reports pertaining to certain allergic reactions to thiomersal primarily in the form of delayed-type local hypersensitivity reactions, including redness and swelling at the injection site. There are also conflicting reports on linking autism to mercury.

2-phenoxyethanol (2-POE) is also known as '1-hydroxy-2-phenoxyethane', '2-hydroxyethyl phenyl ether', 'ethyleneglycol phenyl ether', etc. The safety profile of 2-phenoxyethanol is better than that of mercurial preservatives (e.g. thiomersal). Thus, there is a need of avoiding thiomersal and using 2-phenoxyethanol in the vaccines.

Thus, another preferred embodiment of the invention relates to the use of 2-phenoxyethanol as a preservative in the vaccine composition. According to another preferred embodiment of the invention, the concentration of 2-phenoxyethanol is 5 mg/ml of the vaccine.

Tonicity Modifying Agents

To control to the tonicity of the vaccine composition, it is preferred to include a tonicity modifying agent in the formulation of the vaccine. These agents include but are not limited to salts (examples—NaCl, NaCl, MgCl2, KCl, CaCl2), sugars (examples—dextrose, mannitol, lactose), amino acids (examples—Arginine, Glycine, Histidine) and Polyols (examples—Sucrose, Glycerol, Sorbitol). In a more preferred embodiment, a physiological salt such as sodium salt is used in the formulation of the vaccine. Sodium chloride (NaCl) is most preferably included in the vaccine composition of the invention, pH Modifiers and/or Buffers Various pH modifiers known to person skilled in the art may be used to adjust the pH of the vaccine composition as desired, such as sodium hydroxide or hydrochloric acid. Various buffers such as sodium phosphate, potassium phosphate and citrate buffers may be used in the formulation of the vaccine.

Composition of the Vaccine of the Invention

The composition of the vaccine of the invention is such that the vaccine of the invention is rendered immunogenic by the virtue of the amounts of each of the antigens contained in the vaccine. Each of the antigens in the vaccine of the invention is preferably in amounts so that the combination vaccine when administered to a subject, elicits immune response in the subject, against the said antigen of the composition.

According to one embodiment of the invention, a fully liquid pentavalent vaccine comprises D, T, aP (PT, FHA, PRN), Hib b and IPV (Mahoney type 1, MEF Type 2 and the Saukett type 3), wherein D is present in an amount of about 1-40 Lf, is present in an amount of about 1-25 Lf, PT is present in an amount of about 1-40 ug, FHA is present in an amount of about 1-40 ug and PRN is present in an amount of about 1-15 ug per 0.5 ml, Hib b is present in an amount of about 1-20 ug per 0.5 ml and the Mahoney type 1, MEF type 2 and the Saukett type 3 strains are present in an amount of about 1-50 DU, 1-15 DU and 1-50 DU, respectively per 0.5 ml, to give a stable and immunogenic combination vaccine.

According to one preferred embodiment of the invention, the fully liquid pentavalent vaccine comprises D, T, aP (PT, FHA, PRN), Hib b and IPV wherein D is present in an amount of about 25 Lf, T is present in an amount of about 10 Lf, PT is present in an amount of about 25 ug, FHA is present in an amount of about 25 ug and PRN is present in an amount of about 8 ug per 0.5 ml, Hib b is present in an amount of about 10 ug per 0.5 ml and the Mahoney type 1, MEF type 2 and the Saukett type 3 strains are present in an amount of about 40 DU, 8 DU and 32 DU, respectively per 0.5 ml, such that the said vaccine would be a stable composition and would be immunogenic when administered to a subject.

Another embodiment of the invention provides a fully liquid hexavalent vaccine comprising D, T, aP (PT, FHA, PRN), Hib b, Hep B and IPV (Mahoney type 1, MEF Type 2 and the Saukett type 3), wherein D is present in an amount of about 1-40 Lf, T is present in an amount of about 1-25 Lf, PT is present in an amount of about 1-40 ug, FHA is present in an amount of about 1-40 ug and PRN is present in an amount of about 1-15 ug per 0.5 ml, Hib b is present in an amount of about 1-2.0 ug and Hep B is present in an amount of about 1-25 ug per 0.5 ml and the Mahoney type 1, MEF type 2 and the Saukett type 3 strains are present in an amount of about 1-50 DU, 1-15 DU and 1-50 DU, respectively per 0.5 ml, such that the combination vaccine would be stable and immunogenic when administered to a subject.

According to another preferred embodiment of the invention, there is provided a fully liquid hexavalent vaccine comprising D, T, aP (PT, FHA, PRN), Hib b, Hep B and IPV wherein D is present in an amount of about 25 Lf, T is present in an amount of about 10 Lf, PT is present in an amount of about 25 ug, FHA is present in an amount of about 25 ug and PRN is present in an amount of about 8 ug per 0.5 ml, Hib b is present in an amount of about 10 ug and Hep B is present in an amount of about 10 ug, per 0.5 ml and the Mahoney type 1, MEF type 2 and the Saukett type 3 strains are present in an amount of about 40 DU, 8 DU and 32 DU, respectively per 0.5 mL Such a vaccine would be a stable vaccine capable of eliciting protective immune response against all the antigens of the composition, when administered to a subject.

The invention further relates to a method of inducing immunological response to any of the antigen selected from the group of D, T, P, Hib, Hep or IPV comprising administering immunologically active amount of the vaccine of the invention.

According to another aspect of the invention, the aluminum content ($Al^{+3}$) in the vaccine of the invention may not be more than preferably, 2 mg per 0.5 ml, more preferably 1 mg per 0.5 ml and most preferably 0.8 mg per 0.5 ml.

According to one another aspect of the invention the preferred amount of 2-phenoxyethanol in the combination vaccine of the invention may be 5 mg/ml, Process for Manufacturing of the Vaccine of the Invention One of the aspects of the invention relates to the process for manufacturing of the vaccine of the invention. The immunogenicity, the stability and the maintenance of the right form of the antigens in the immunogenic composition may depend on the way the composition has been formulated. This may include the sequence of addition of the antigens, the use of the specific adjuvants for certain antigens, the use of various parameters including agitation, temperature and pH.

One of the embodiments of the invention relates to the process of manufacturing the fully liquid stable pentavalent vaccine comprising Diptheria (D), Tetanus (T), Acellular pertussis (aP), *Haemophilus influenzae* (Hib) and IPV antigens comprising the steps of:
a) preparing a component 1 comprising i) Diphtheria (D) ii) Tetanus (T) and iii) Acellular Pertussis (aP) antigens
b) adding the component I to *Haemophilus influenzae* (Hib) antigen preparation to obtain a mixture
c) adding above mixture to poliovirus (IPV) antigens
with the proviso that the Hib is not substantially adsorbed onto any adjuvant.

According to one preferred embodiment of the invention the D, T and the aP antigens are adsorbed on to aluminum phosphate.

One of the embodiments of the invention relates to the preparation of the component I which comprises the following steps:
a) transferring Diphtheria and Tetanus antigen preparations along with the aluminium phosphate gel, saline solution and 2-phenoxyethanol (2-POE) in a vessel
b) transferring PT, FHA and PRN antigen preparations under stirring to the above vessel to obtain a mixture
c) adding saline and 2-POE to the said vessel, checking the pH of the above mixture, and adjusting it in a range of 6.0-7.0

The process further relates to the mixing of the Hib and IPV antigens with the component I of the vaccine of the invention which comprises the step of transferring the above mixture comprising the D, T and the aP antigens to Hib antigen preparation to obtain another mixture and then mixing this mixture with the IPV antigen preparation, checking the pH, and adjusting it in a range of 6.0-7.0

The invention further relates to another preferred embodiment of the invention which provides a process for manufacturing the fully liquid stable hexavalent vaccine comprising Diptheria (D), Tetanus (T), Acellular pertussis (aP), *Haemophilus influenzae* (Hib), Hepatitis and IPV antigens, comprising the steps of:
a) preparing a component I comprising i) Diphtheria (D) ii) Tetanus (T) and iii) Acellular Pertussis (aP) antigens
b) preparing a component II comprising Hepatitis (Hep) antigen
c) combining components I and II to form a mixture,
d) adding the above mixture to Hib and IPV antigens.

with the proviso that the D, T and the aP antigens have been adsorbed on to aluminum phosphate and the Hep antigen is adsorbed on to aluminum hydroxide.

According to another preferred aspect of the invention, the preparation of the component I comprise the following steps:
a) transferring Diphtheria and Tetanus antigen preparations along with the aluminium phosphate gel, saline solution and 2-phenoxyethanol (2-POE) in a vessel
b) transferring PT, FHA and PRN antigen preparations under stirring to the above vessel
c) adding saline and 2-POE to the said vessel, checking the pH, and adjusting it in a range of 6.0-7.0

The process further comprises the preparation of the component I of the vaccine of the invention comprises the following steps:
a) transferring aluminium Hydroxide gel into a vessel,
b) transferring Hep antigen preparation to the vessel
c) adding saline and 2-POE preparation under stirring, checking the pH, and adjusting it in a range of pH 6.0-7.0

Further the process relates to the mixing of the component I and II of the vaccine of the invention, comprising the step of transferring the contents of component II to the component I to obtain a mixture.

The process further involves mixing of the Hib and IPV antigens with the mixture obtained above, that comprises the step of mixing the said above mixture with the Hib antigen preparation to obtain another mixture and further mixing this mixture with the IPV antigen preparation, checking the pH, and adjusting it in a range of 6.0-7.0

According to one preferred embodiment of the invention, the stirring as mentioned in any of the steps above is done at 150 rpm at 25±2° C. for about 30 minutes to 2 hours.

The following examples are used to further illustrate the present invention and advantages thereof. The following specific examples are given with the understanding that these are intended to be illustration without serving as a limitation on the scope of present invention.

EXAMPLE I

This Example Gives the Composition and the Process of Manufacturing of the Pentavalent Vaccine as Per One of the Aspect of the Invention A] Composition of the Pentavalent Vaccine as Per the Invention is as Under Each 0.5 ml vaccine comprises the following:

TABLE 1

| COMPONENTS | AMOUNT |
| --- | --- |
| Diphtheria Toxoid[1] (DT) | 25 Lf |
| Tetanus Toxoid[1] (TT) | 10 Lf |
| Acellular Pertussis[1] (aP) | |
| Pertussis Toxoid (PT) | 25 µg |
| Filamentous Hemagglutinin (FHA) | 25 µg |
| Pertactin (PRN) | 8 µg |
| *Haemophilus influenzae* (Hib) b (capsular polysaccharide) antigen | 10 µg |
| Inactivated Polio Virus (IPV) | |
| Polio type 1 | 40 D units |
| Polio type 2 | 8 D units |
| Polio type 3 | 32 D units |

TABLE 1-continued

| COMPONENTS | AMOUNT |
| --- | --- |
| Other Ingredients: | |
| Aluminum Content | 0.60 mg of Al$^{+3}$ (as Aluminum Phosphate) |
| 2-phenoxy ethanol | 2.5 mg |
| Saline solution | q.s. |

[1]on aluminium phosphate
q.s.—quantity sufficient

B] The Process of Manufacturing of Pentavalent Vaccine as Per the Invention is as Under:

1. Formulation Procedure for Component 1

The Diphtheria and Tetanus antigen preparations along with the aluminium phosphate gel, saline solution and 2-POE were transferred to a vessel, followed by the PT, FHA and PRN antigen preparations. Further saline and 2-phenoxyethanol (2-POE) were mixed to the mixture in the above said vessel; the pH was checked and adjusted to fall in a range of pH 6.0-7.0.

2. Addition of Hib b and IPV Bulk

The contents of the components I were mixed with the Hib b antigen preparation to obtain another mixture which was then mixed with the IPV antigen preparation under stirring, to obtain a pentavalent vaccine. The was checked and adjusted to fall in a range of 60-7.0.

EXAMPLE II

This Example Gives the Composition and the Process of Manufacturing of the Hexavalent Vaccine as Per One of the Aspect of the Invention A] Composition of Hexavalent Vaccine as Per the Invention is as Under:

Each 0.5 ml vaccine comprises the following:

TABLE 2

| COMPONENTS | AMOUNT |
| --- | --- |
| Diphtheria Toxoid[1] (DT) | 25 Lf |
| Tetanus Toxoid[1] (TT) | 10 Lf |
| Acellular Pertussis[1] (aP) | |
| Pertussis Toxoid (PT) | 25 μg |
| Filamentous Hemagglutinin (FHA) | 25 μg |
| Pertactin (PRN) | 8 μg |
| *Haemophilus influenzae* (Hib) b (capsular polysaccharide) antigen | 10 μg |
| Hepatitis (Hep) B Surface Antigen (HBsAg)[2] | 10 μg |
| Inactivated Polio Virus (IPV) | |
| Polio type 1 | 40 D units |
| Polio type 2 | 8 D units |
| Polio type 3 | 32 D units |
| Other Ingredients: | |
| Aluminum Content | 0.60 mg of Al$^{+3}$ (as Aluminum Phosphate) 0.20 mg of Al$^{+3}$ (as Aluminum Hydroxide) |
| 2-phenoxy ethanol | 2.5 mg |
| Saline solution | q.s. |

[1]on aluminium phosphate;
[2]on aluminium Hydroxide
q.s.—quantity sufficient

B] The Process of Manufacturing of Hexavalent Vaccine as Per the Invention is as Under:

1. Formulation Procedure for Component I

The Diphtheria and Tetanus antigen preparations along with the aluminium phosphate gel, saline solution and 2-phenoxyethanol (2-POE) were transferred to a vessel, followed by the PT, FHA and PRN antigen preparations. Further saline and 2-POE were mixed to the mixture in the above said vessel; the pH was checked and adjusted to fall in a range of pH 6.0-7.0.

2. Formulation Procedure for Component II

Aluminium Hydroxide gel was taken in a vessel. Hep B antigen preparation was mixed to obtain a mixture. Further saline and 2-POE preparation was mixed with the said mixture comprising Hep B antigen, the pH was checked and adjusted to fall in a range of pH 6.0-7.0

3. Mixing of Component I and Component II

This step was carried out by transferring the contents of the component II to the component I to obtain a mixture 4. Addition of Hib b and IPV Bulk The above mixture comprising the components I and II were mixed with the 1-lib antigen preparation to obtain another mixture which was then mixed with the IPV antigen preparation under stirring, to obtain a hexavalent vaccine. The pH was checked and adjusted to fall in a range of 6.0-7.0.

EXAMPLE III

This Example Gives a Brief on the In-Vivo Potency Testing Carried Out for Diphtheria, Tetanus, Whole Cell Pertussis, *Haemophilus influenzae* Type (Hib) b, Hepatitis B and Inactivated Polio Antigens and the Stability Data or the Potency for the Same A] In-Vivo Potency Testing Carried Out for Diphtheria, Tetanus, Whole Cell Pertussis, *Haemophilus Influenzae* Type (Hib) b, Hepatitis B and Inactivated Polio Antigens 1. Diphtheria Toxoid

| | |
| --- | --- |
| Animal species required | Guinea pigs |
| No. of animals required for 1 batch | 116 (48 for test, 48 for reference & 20 for LD$_{50}$) |
| Route of vaccine administration | Subcutaneous |
| Volume of injection | 1.0 ml |
| No. of days animals are housed | 28 |

Potency of Diphtheria toxoid was determined in Guinea pigs by lethal challenge method. In this method, three dilutions each of the test and the reference vaccine were prepared such that the middle dilution contains the ED$_{50}$ dose that saves at least or more than 50% of the test animals. Sixteen Guinea pigs for every dilution of test vaccine & reference vaccine were inoculated and after 28 days the test animals were subcutaneously challenged with Diphtheria toxin containing 100 LD$_{50}$. A group of twenty Guinea pigs were kept unimmunized for the titration of the Diphtheria Toxin & this group of guinea pigs were inoculated with different dilutions of Diphtheria toxin, 5 guinea pigs for every dilution. Test was completed in 33 days. Further calculations were done by using PROBIT. The sample passes the diphtheria potency test if it contains ≥30 IU/Single Human Dose.

The test vaccine should fulfill linearity & parallelism with reference vaccine.

Fiducial limit of estimated potency should lie between 50 to 200%.

Estimated potency should not be less than 30 I.U. per single human dose.

The limit of 95% confidence interval of estimate of potency should be within 50-200% unless the lower limit of the 95% confidence interval of the estimated potency should be greater than 30 I.U. per dose 2. Tetanus Toxoid

| | |
|---|---|
| Animal species required | Swiss albino mice |
| No. of animals required for 1 batch | 116 (48 for test, 48 for reference & 50 for $LD_{50}$) |
| Route of vaccine administration | Subcutaneous |
| Volume of injection | 0.5 ml |
| No. of days animals are housed | 28 |

Potency test of Tetanus toxoid was determined in Swiss mice by lethal challenge method. In the test, three dilutions each of the test and the reference vaccine were prepared such that the middle dilution contains the $ED_{50}$ dose that saves at least or more than 50% of the test animals. A group of sixteen Swiss mice for every dilution of test vaccine as well as reference vaccine was inoculated and after 28 days of housing the test animals were challenged with Tetanus toxin containing 100 $LD_{50}$. A group of twenty Swiss mice were kept unimmunized for the titration of the Tetanus Toxin & were inoculated with 5 mice for 4 dilutions of $LD_{50}$ titration. Test was completed in 33 days. Further calculations were carried by using PROBIT. Potency sample passes the tetanus potency test if it contains ≥60 IU/Single Human Dose.

The test vaccine should fulfill linearity & parallelism with reference vaccine.

Fiducial limit of estimated potency should lie between 50 to 200%.

Estimated potency should not be less than 60 I.U. per single human dose.

The limit of 95% confidence interval of estimate of potency should be within 50-200% unless the lower limit of the 95% confidence interval of the estimated potency is greater than 60 I.U. per dose.

3. Acellular Pertussis (aP) Antigen

| | |
|---|---|
| Animal species required | Swiss mice |
| No. of animals required for 1 batch | 24 |
| Route of vaccine administration | Subcutaneous |
| Volume of injection | 0.5 ml |
| No. of days animals are housed | 35 |

Potency of aP antigen was determined in Swiss mice by ELISA method. Three dilutions (Neat, 1:5, 1:25) of test vaccine were made. Three groups of 8 Swiss mice were selected & each group was immunized by their respective dilutions. Each mouse of test group was subcutaneously injected with 0.5 ml of diluted vaccines. Final blood collection was done on $35^{th}$ day. Serum samples were tested for antibody against Hib by ELISA method. The sample passes the aP potency test if ≥70% mice in test group are seroconverted.

4. *Hemophilus influenzae* type b antigen

| | |
|---|---|
| Animal species required | Swiss mice |
| No. of animals required for 1 batch | 16 (8 for immunization, 8 serving as control) |
| Route of vaccine administration | Subcutaneous |
| Volume of injection | 0.5 ml |
| No. of days animals are housed | 35 |

Potency test of Hib b antigen was carried out in Swiss mice by ELISA method. In this test two groups (test and control group) each of 8 Swiss mice were selected. Each mouse of test group was subcutaneously injected with 0.5 ml of 1:4 diluted vaccines and control group was left uninoculated. Booster dose was given on $10^{th}$ and $20^{th}$ day and final blood collection is done on $35^{th}$ day. Serum samples were tested for antibody against Hib by ELISA method. The sample passes the Hib potency test if ≥50% mice in test group are seroconverted.

5. Hepatitis B Surface Antigen

| | |
|---|---|
| Animal species required | Balb C mice |
| No. of animals required for 1 batch | 110 (50 for sample, 50 for reference, 10 for Placebo) |
| Route of vaccine administration | Intraperitoneal |
| Volume of injection | 1.0 ml |
| No. of days animals are housed | 28 |

Potency test of Hepatitis B Surface Antigen was carried out in Balb/C mice. In this test, five two-fold dilutions each of reference and test vaccine were prepared and ten mice were intraperitoneally inoculated per dilution. Ten mice were inoculated with diluent and served as placebo. The inoculated mice were bled on $28^{th}$ day of inoculation and sera was separated taking care that no hemolysis occurs. The sera samples were tested for antibody titer against Hepatitis B by ELISA. The sample passes the Hepatitis B potency test if the upper limit of its relative potency ≥1.

6. Inactivated Polio Vaccine (IPV)

| | |
|---|---|
| Animal species required | Wistar rats |
| No. of animals required for 1 batch | 100 (50 for test vaccine, 50 for reference Vaccine) |
| Route of vaccine administration | Intramuscular |
| Volume of injection | 0.5 ml |
| No. of days animals are housed | 21 |

Potency test of IPV was carried out in RIVM TOX rats. Five three fold dilutions each of reference and test vaccine were prepared and ten rats were intramuscularly injected with 0.5 ml of each dilution. Test animals were bled 21 days after the immunization and serum samples were collected carefully avoiding lysis of RBCs. Each serum sample was tested for antibody titer against type 1, type 2 and type 3 serotypes of Polio virus by serum neutralization test.

The test is not valid unless;

the median effective dose (ED50) for both the test and reference vaccines lies between the smallest and the largest doses given to the animals;

the statistical analysis shows no significant deviation from linearity or parallelism;

the fiducial limits of the estimated relative potency fall between 25% and 400% of the estimated potency.

B] Stability Data or the Potency of the Antigens in the Vaccine of the Invention The tests were carried out as given in Example III A] for all the antigens of the hexavalent vaccine of the Example II. The results are as tabulated in the table below.

TABLE 3

| Sr. No. | Components | | Acceptance Limits | Long Term Study (5° C. ± 3° C.) 6 months |
|---|---|---|---|---|
| 1 | Acellular Pertussis (aP) (Potency) | | ≥70% | 100% |
| 2 | Hib b (capsular polysaccharide) antigen (Potency) | | ≥50% | 100% |
| 3 | Hepatitis (Hep) B surface antigen (HBsAg) (Potency) | | ≥1.0 | 1.18 |
| 4 | Inactivated Polio Virus (IPV) (Potency) | Type 1 Type 2 Type 3 | Potency of the test Vaccine should not be less than the Ref. Vaccine | Complies Complies Complies |

Thus, it can be seen that even after the long term storage of the vaccine at 5±3° C., the vaccine antigens are still potent/have immunogenicity above the acceptance limits.

The invention claimed is:

1. A fully liquid stable combination vaccine comprising Diphtheria (D), Tetanus (T), acellular pertussis (aP), *Haemophilus influenzae* (Hib) and Poliovirus (IPV) antigens, wherein Hib is not substantially adsorbed on to any adjuvant.

2. The vaccine as claimed in claim 1, wherein Hib is conjugated to a carrier protein selected from a group comprising tetanus toxoid, diphtheria toxoid, CRM 197 and outer membrane protein of *Neisseria meningitides*, or any other known carrier.

3. The vaccine as claimed in claim 1, wherein the Hib antigen is a capsular polysaccharide of the Hib b strain.

4. The vaccine as claimed in the claim 1, wherein the IPV antigens are Salk strains selected from the group of Mahoney type 1, MEF Type 2 and the Saukett type 3 or Sabin strains selected from the group of Sabin 1 or 2.

5. The vaccine as claimed in the claim 1, wherein the D, T and the aP antigens are adsorbed on to aluminum phosphate.

6. The vaccine as claimed in claim 1, wherein the aP comprises at least one or more antigens from the group of Pertussis toxoid (PT), Filamentous hemagglutinin (FHA), Pertactin (P69 or PRN) and Fimbrial proteins (FIM 1, 2 and 3).

7. The vaccine as claimed in claim 1, comprising D, T, aP (PT, FHA, PRN), Hib b and IPV (Mahoney type 1, MEF Type 2 and the Saukett type 3), wherein D is present in an amount of about 1-40 Lf, T is present in an amount of about 1-25 Lf, PT is present in an amount of about 1-40 ug, FHA is present in an amount of about 1- 40 ug and PRN is present in an amount of about 1-15 ug per 0.5 ml, Hib b is present in an amount of about 1-20 ug per 0.5 ml and the Mahoney type 1, MEF type 2 and the Saukett type 3 strains are present in an amount of about 1-50 DU, 1-15 DU and 1-50 DU, respectively per 0.5 ml.

8. The vaccine as claimed in claim 7, comprising D, T, aP (PT, FHA, PRN), Hib b and IPV wherein D is present in an amount of about 25 Lf, T is present in an amount of about 10 Lf, PT is present in an amount of about 25 ug, FHA is present in an amount of about 25 ug and PRN is present in an amount of about 8 ug per 0.5 ml, Hib b is present in an amount of about 10 ug per 0.5 ml and the Mahoney type 1, MEF type 2 and the Saukett type 3 strains are present in an amount of about 40 DU, 8 DU and 32 DU, respectively per 0.5 ml.

9. A fully liquid stable combination vaccine comprising Diphtheria (D), Tetanus (T), acellular pertussis (aP), *Haemophilus influenzae* (Hib) and Hepatitis (Hep) and Poliovirus (IPV) antigens, wherein the D, T and the aP antigens are adsorbed on to aluminum phosphate and Hep antigen is adsorbed on to aluminum hydroxide.

10. The vaccine as claimed in claim 9, wherein Hib is conjugated to a carrier protein selected from a group comprising tetanus toxoid (TT), diphtheria toxoid (DT), CRM 197 and outer membrane protein of *Neisseria meningitides*, or any other known carrier.

11. The vaccine as claimed in the claim 9, wherein the Hib antigen is not substantially adsorbed on to any adjuvant.

12. The vaccine as claimed in claim 9, wherein the Hib antigen is a capsular polysaccharide of the Hib b strain.

13. The vaccine as claimed in the claim 9, wherein the Hep antigen is a surface antigen of the Hep B strain.

14. The vaccine as claimed in the claim 9, wherein the IPV antigens are Salk strains selected from the group of Mahoney type 1, MEF Type 2 and the Saukett type 3 or Sabin strains selected from the group of Sabin 1 or 2.

15. The vaccine as claimed in claim 9, wherein the aP comprises at least one antigen from the group of Pertussis toxoid (PT), Filamentous hemagglutinin (FHA), Pertactin (P69 or PRN) and Fimbrial proteins (FIM 1,2 and 3).

16. The vaccine as claimed in claim 9, comprising D, T, aP (PT, FHA, PRN), Hib b, Hep B and IPV (Mahoney type 1, MEF Type 2 and the Saukett type 3), wherein D is present in an amount of about 1-40 Lf, T is present in an amount of about 1-25 Lf, PT is present in an amount of about 1-40 ug, FHA is present in an amount of about 1-40 ug and PRN is present in an amount of about 1-15 ug per 0.5 ml, Hib b is present in an amount of about 1-20 ug and Hep B is present in an amount of about 1-25 ug per 0.5 ml and the Mahoney type 1, MEF type 2 and the Saukett type 3 strains are present in an amount of about 1-50 DU, 1-15 DU and 1-50 DU, respectively per 0.5 ml.

17. The vaccine as claimed in claim 16, comprising D, T, aP (PT, FHA, PRN), Hib b, Hep B and IPV wherein D is present in an amount of about 25 Lf, T is present in an amount of about 10 Lf, PT is present in an amount of about 25 ug, FHA is present in an amount of about 25 ug and PRN is present in an amount of about 8 ug per 0.5 ml, Hib b is present in an amount of about 10 ug and Hep B is present in an amount of about 10 ug, per 0.5 ml and the Mahoney type 1, MEF type 2 and the Saukett type 3 strains are present in an amount of about 40 DU, 8 DU and 32 DU, respectively per 0.5 ml.

18. A method of inducing immunological response to any of the antigens selected from the group of D, T, aP, Hib, Hep or IPV comprising administering immunologically active amount of the combination vaccine as claimed in claim 9 to a subject.

19. A process for manufacturing a fully liquid stable combination vaccine, comprising the steps of:
  a) adding, to a component I comprising i) Diphtheria (D) ii) Tetanus (T) and iii) acellular Pertussis (aP) antigens, *Haemophilus influenzae* (Hib) antigen preparation to obtain a mixture, and
  b) adding the mixture to poliovirus (IPV) antigen preparation with the proviso that the Hib is not substantially adsorbed onto any adjuvant.

20. The process as claimed in claim 19, wherein the D, T and the aP antigens are adsorbed on to aluminum phosphate.

21. The process as claimed in claim 19, wherein the process further comprises the step of adding 2- phenoxyethanol (2-POE) as the preservative to the formulation.

22. The process as claimed in claim 19, wherein the preparation of the component I comprises the following steps:
  a) transferring Diphtheria and Tetanus antigen preparations along with an aluminum phosphate gel, saline solution and 2-POE in a vessel, b) transferring Pertussis toxoid (PT), Filamentous hemagglutinin (FHA) and Pertactin (PRN) antigen preparations to the vessel, and c) checking the pH of the mixture resulting from a) and b), and adjusting the pH of the mixture resulting from a) and b) in a range of 6.0-7.0.

23. A process for manufacturing a fully liquid stable combination vaccine, comprising the steps of:

a) combining a component I comprising i) Diphtheria (D) ii) Tetanus (T) and iii) acellular Pertussis (aP) antigens, and a component II comprising Hepatitis (Hep) antigen, to form a mixture, and b) adding the mixture to Hib and IPV antigen preparation with the proviso that the D, T and the aP antigens have been adsorbed on to aluminum phosphate and the Hep antigen is adsorbed on to aluminum hydroxide.

24. The process as claimed in claim 23, wherein the process further comprises the step of adding 2- phenoxyethanol (2-POE) as the preservative to the formulation.

25. The process as claimed in claim 23, wherein the preparation of component I comprises the following steps:

a) transferring Diphtheria and Tetanus antigen preparations along with the aluminum phosphate gel, saline solution and 2-POE in a vessel, b) transferring Pertussis toxoid (PT), Filamentous hemagglutinin (FHP) and Pertactin (PRN) antigen preparations to the vessel, and c) checking the pH of the mixture resulting from a) and b), and adjusting the pH of the mixture resulting from a) and b) in a range of 6.0-7.0.

26. The process as claimed in claim 23, wherein the preparation of component II comprises the following steps:

a) transferring aluminum hydroxide gel into a vessel, b) transferring Hep antigen preparation to the vessel, and c) adding saline and 2-POE preparation, checking the pH of the mixture resulting from a) and b), and adjusting the pH of the mixture resulting from a) and b) in a range of pH 6.0-7.0.

27. The process as claimed in claim 23, wherein the combining of the component I and II comprises the step of transferring the contents of component II to the component I to obtain a mixture.

28. A method of inducing immunological response to any of the antigens selected from the group of D, T, aP, Hib, or IPV comprising administering immunologically active amount of the combination vaccine as claimed in claim 1 to a subject.

\* \* \* \* \*